(12) United States Patent
Shin et al.

(10) Patent No.: US 11,559,659 B2
(45) Date of Patent: Jan. 24, 2023

(54) MEDICAL DEVICE FOR PUNCTURING

(71) Applicant: STARMED CO., LTD., Goyang-si (KR)

(72) Inventors: Kyung Hoon Shin, Gimpo-si (KR); Dong Un Kim, Gimpo-si (KR); Yo Han Lee, Gimpo-si (KR)

(73) Assignee: STARMED CO., LTD., Goyang-si (KR)

( * ) Notice: Subject to any disclaimer, the term of this patent is extended or adjusted under 35 U.S.C. 154(b) by 345 days.

(21) Appl. No.: 17/065,943

(22) Filed: Oct. 8, 2020

(65) Prior Publication Data

US 2021/0121662 A1    Apr. 29, 2021

(30) Foreign Application Priority Data

Oct. 24, 2019    (KR) .................. 10-2019-0132864

(51) Int. Cl.
| | |
|---|---|
| A61M 25/00 | (2006.01) |
| A61B 17/34 | (2006.01) |
| A61B 18/14 | (2006.01) |
| A61B 90/00 | (2016.01) |
| A61B 17/00 | (2006.01) |
| A61B 18/00 | (2006.01) |
| A61M 5/00 | (2006.01) |

(52) U.S. Cl.
CPC ......... *A61M 25/0082* (2013.01); *A61B 17/34* (2013.01); *A61B 18/1492* (2013.01); *A61M 25/007* (2013.01); *A61B 2017/00247* (2013.01); *A61B 2017/00867* (2013.01); *A61B 2018/00595* (2013.01); *A61B 2090/3966* (2016.02); *A61M 5/007* (2013.01)

(58) Field of Classification Search
CPC ...... A61B 2017/00247; A61M 25/007; A61M 25/0082
See application file for complete search history.

(56) References Cited

U.S. PATENT DOCUMENTS

| | | |
|---|---|---|
| 9,743,984 B1 | 8/2017 | Clevenger et al. |
| 2008/0161795 A1 | 7/2008 | Hong et al. |
| 2016/0158509 A1 | 6/2016 | Brutlag et al. |

FOREIGN PATENT DOCUMENTS

| | | |
|---|---|---|
| JP | 2011-500156 A | 1/2011 |
| JP | 2016-152938 A | 8/2016 |
| JP | 2019-072522 A | 5/2019 |
| WO | 00/25669 A1 | 5/2000 |

*Primary Examiner* — Deanna K Hall
(74) *Attorney, Agent, or Firm* — Bridgeway IP Law Group, PLLC; Jihun Kim

(57) ABSTRACT

A medical device includes: a tube through which fluid flows; a handle part coupled to a proximal end part of the tube; an electrode tip coupled to a distal end part of the tube; a fluid injection part configured to inject fluid into the tube; one or more openings formed in the tube; and a guide member disposed in the tube, and having an inclined part to guide the direction of the fluid sprayed out through the opening.

12 Claims, 7 Drawing Sheets

MEDICAL DEVICE FOR PUNCTURING

BACKGROUND

1. Technical Field

The present disclosure relates to a medical device, and more particularly, to a medical device capable of performing puncturing and injecting fluid.

2. Related Art

Various types of puncturing devices are used to form a punctured portion or channel through the skin tissue. The devices may use various puncturing units, for example, mechanical, electrical or optical puncturing units. Typically, the devices are inserted into the body of a patient through a pipe-shaped device such as a dilator or sheath. In a plurality of applications, users may want to insert or extract fluid through the device before, after or during the puncturing operation.

RELATED ART DOCUMENT

Patent Document (Patent Document 0001) Japanese Patent Application No. 2016-152938 (published on Aug. 25, 2016)
(Patent Document 0002) US Patent Application No. 2016-0158509 (published on Jun. 9, 2016)

SUMMARY

Various embodiments are directed to a medical device capable of performing puncturing and injecting fluid.

Technical problems to be solved through the present disclosure are not limited to the above-described technical problems, and other technical problems which are not described may be clearly understood from the following descriptions by those skilled in the art to which the present disclosure pertains.

In an embodiment, a medical device may include: a tube through which fluid flows; a handle part coupled to a proximal end part of the tube; an electrode tip coupled to a distal end part of the tube; a fluid injection part configured to inject fluid into the tube; one or more openings formed in the tube; and a guide member disposed in the tube, and having an inclined part to guide the direction of the fluid sprayed through the opening.

The guide member may be extended from the electrode tip to the position where the opening is formed.

The guide member may be formed as one body with the electrode tip.

The inclined part of the guide member may be conical.

The inclined part of the guide member may have an inclination of 20 to 60° with respect to the central axial line of the tube.

The guide member may include: a cylinder part; and the inclined part tapered from the cylinder part.

The inclined part may be extended from one end of the opening to the center.

The electrode may be formed of an X-ray opaque material.

The tube may be coated with an insulator through dip coating, spray coating or heat shrink tubing.

The medical device may further include a wire having one end connected to the electrode tip or the distal end part of the tube and the other end extended to the handle part.

The medical device may further include a wire manipulation part slidably or rotatably installed on the handle part. The other end of the wire may be connected to the wire manipulation part.

At least a section of the tube may be tapered so that the proximal end part of the tube has a smaller thickness than the distal end part of the tube.

The tube may include a first tube to which the handle part is coupled and a second tube to which the electrode tip is coupled. The first tube may be formed of a rigid material, and the second tube is formed of a flexible material.

In accordance with the embodiments of the present disclosure, the puncturing operation and the fluid injection can be performed together, and the fluid injection direction can be guided by the guide member. Thus, the fluid can be effectively sprayed forward without interference.

Furthermore, the medical device can secure visibility such that a user can check the position of the electrode tip, which makes it possible to facilitate the puncturing operation.

Furthermore, as the tube is coated with an insulator through dip coating, spray coating or heat shrink tubing, the coating of the tube can be prevented from being damaged by an external impact or heat generated during cauterization, which makes it possible to improve the level of completion and durability.

The effects of the present disclosure are not limited to the above-described effects, but it should be noted that the effects include all effects which can be inferred from the detailed descriptions of the present disclosure or components described in claims of the present disclosure.

DETAILED DESCRIPTION

Figure 1:
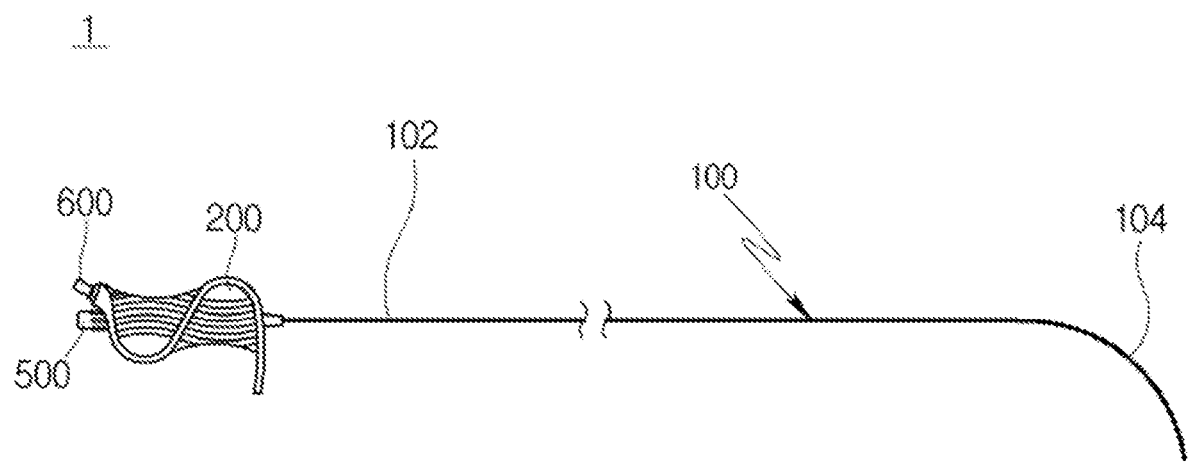
FIG. 1 is a front view illustrating a medical device in accordance with an embodiment of the present disclosure.

Hereafter, a medical device in accordance with a preferred embodiment of the present disclosure will be described with reference to the accompanying drawings.

The terms described below may be defined in consideration of functions in the present disclosure, and changed according to the practice or the intention of a user or operator. The following embodiments do not limit the claims of the present disclosure, but are only examples of components described in claims of the present disclosure.

In order to clearly describe the present disclosure, parts which are not related to the descriptions are omitted. Throughout the specification, the same or similar components will be represented by like reference numerals. Throughout the specification, when a part "includes or comprises" a component, it may indicate that the part does not exclude the component, but can further include or comprise another component, unless referred to the contrary.

Figure 2:
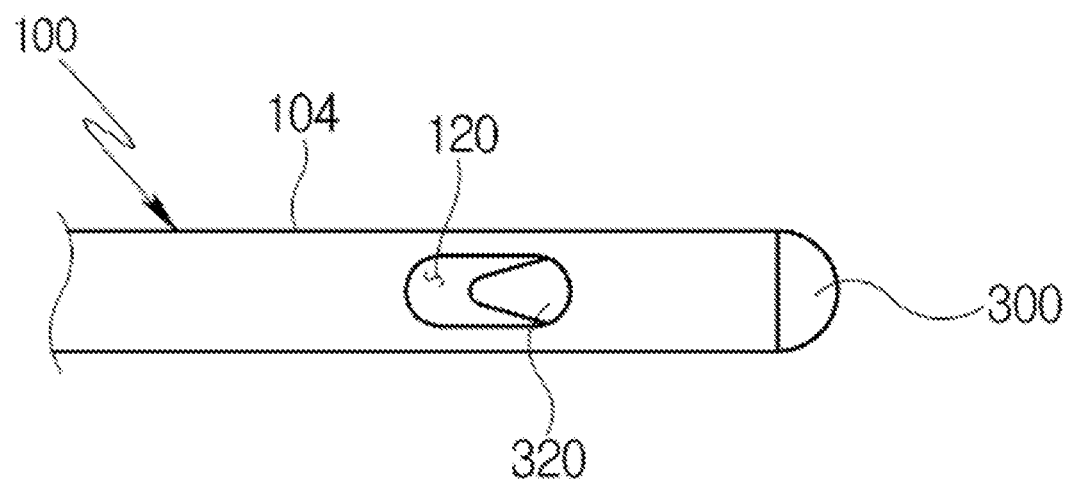
FIG. 2 is an expanded front view illustrating a distal end part of FIG. 1.
Figure 3:
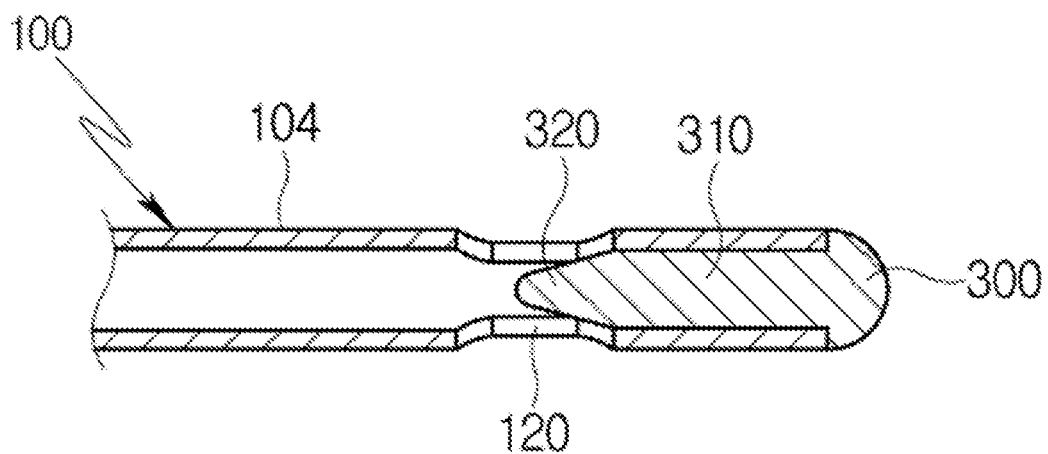
FIG. 3 is a cross-sectional view of FIG. 2.
Figure 4:
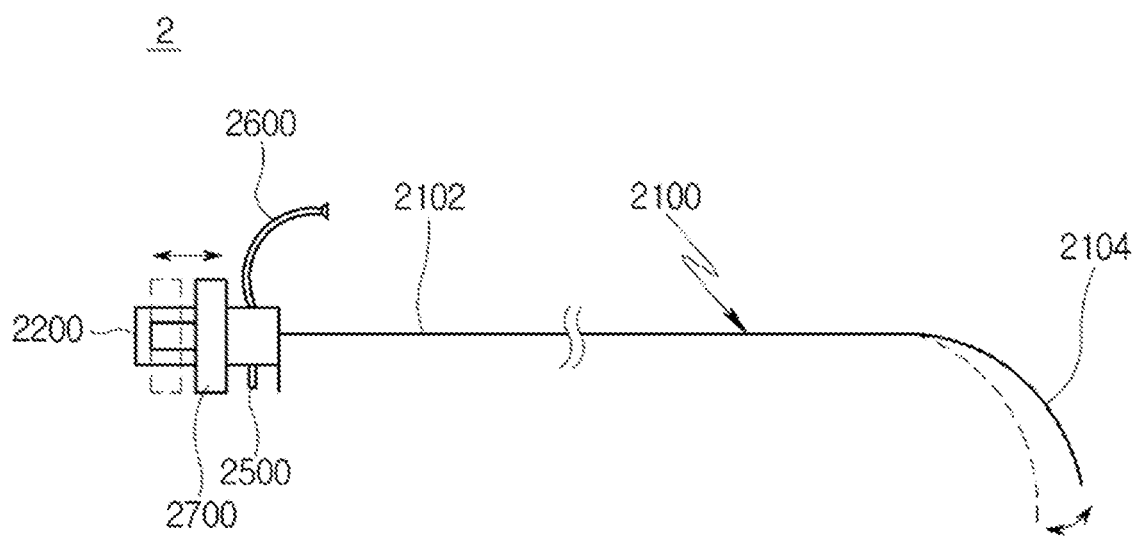
FIG. 4 is a front view illustrating a medical device in accordance with another embodiment of the present disclosure.

First, a medical device 1 in accordance with a first embodiment of the present disclosure will be described with reference to FIGS. 1 to 3.

The medical device 1 in accordance with the first embodiment of the present disclosure may include a tube 100, a handle part 200, an electrode tip 300, a fluid injection part 500, an electrical energy supply part 600 and a guide member.

The tube 100 may serve to transfer fluid and pass fluid therethrough, and is extended to have a proximal end part 102 and a distal end part 104. The proximal end part 102 refers to an end part close to a user who uses the medical device, and the distal end part 104 refers to an end part remote from the user. The tube 100 may be formed as one pipe, and constituted by a plurality of pipes which are connected to one another to form one tube. For example, the tube 100 may be constituted by two pipes which are connected by inserting a predetermined portion of one pipe into the other pipe.

The handle part 200 is coupled to the proximal end part 102 of the tube, and the electrode tip 300 is coupled to the distal end part 104 of the tube. The handle part 200 corresponds to a part which is located outside the body of a patient and held or manipulated by the user, when the medical device is used. The electrode tip 300 serves to receive electrical energy and form a puncture by cauterizing an interior part of the body of the patient, and is coupled to the distal end part 104 such that at least a part thereof protrudes from the distal end part 104 of the tube. In the present embodiment, the electrode tip 300 has a round head, and is coupled to the distal end part 104 such that the round head protrudes from the distal end part 104 of the tube.

The fluid injection part 500 corresponds to a part for injecting fluid into the tube 100, and the user may connect a syringe or the like to the fluid injection part 500 in order to inject fluid. In the present embodiment, the tube 100 is extended to the inside of the handle part 200, and the fluid injection part 500 is also extended to the inside of the handle part 200 so as to communicate with the tube 100.

The electrical energy supply part 600 corresponds to a part for supplying electrical energy to the electrode tip 300, and RF (Radio Frequency) electrical energy generated from an RF generator may be supplied to the electrode tip 300 through the electrical energy supply part 600. The RF generator may generate a radio frequency suitable for puncturing an interior part of the body of the patient. For example, the RF generator may operate in the range of 200 kHz to 3.3 MHz.

Specifically, the electrical energy supply part 600 may be extended to the inside of the handle part 200, and electrically connected to the tube 100. For example, the electrical energy supply part 600 may be a jack which can be electrically connected to a plug which is electrically connected to the RF generator, and the jack and the tube 100 may be directly connected to each other or connected through a separate conductive wire. Therefore, RF electrical energy may be transferred from the electrical energy supply part 600 to the electrode tip 300 through the tube 100, and applied to the interior part of the body of the patient through the electrode tip 300 so as to form a puncture through the interior part. For this operation, the tube 100 in accordance with the present embodiment has biocompatibility, and may be formed of an electro-conductive material like the electrode tip 300. The biocompatibility indicates a material suitable for being used in the body of a patient during a surgical treatment. The material of the tube 100 includes stainless steel, copper, titanium and nickel titanium alloy (e.g. NITINOL), for example. However, the present disclosure is not limited thereto. When the tube is not formed of a conductive material (for example, when the tube is formed of plastics), a separate wire for transferring electrical energy from the electrical energy supply part to the electrode tip may be further provided.

When the tube 100 is formed of a conductive material, the tube 100 may be coated with an insulator. In this case, dip coating, spray coating or heat shrink tubing may be applied.

The dip coating refers to a coating method which dips a material (tube) into a coating solution and takes the material out of the coating solution at predetermined speed in order to cure the coating solution on the material, and the spray coating refers to a coating method which sprays a coating solution onto the surface of a material through a spray nozzle in order to coat the material with the coating solution. The heat shrink tubing refers to a method using a tube which can be shrunken through heat without a coating solution. According to the heat shrink tubing, a heat shrink tube is put on a material and shrunken through heat which is applied at predetermined temperature by a heat gun, in order to coat the material with the heat shrink tube. The above-described coating methods have advantages in that the resultant materials (tubes) all have flat surfaces and excellent insulating properties.

As the tube is coated in such a manner, the coating may be prevented from being damaged by an external impact or heat generated during cauterization, which makes it possible to improve the level of completion and durability. For example, the insulator may include any one of PTFE (polytetrafluoroethylene), parylene, polyimides, PET (polyethylene terephthalate), polyether block amide, and polyether ether ketone or combinations thereof.

Next, a structure for spraying fluid, injected into the tube 100 through the fluid injection part 500, to the outside of the tube 100 will be described with reference to FIGS. 2 and 3.

The tube 100 may have one or more openings 120, and the fluid within the tube 100 may be sprayed to the outside through the openings 120. In the present embodiment, the two openings 120 may be formed at the distal end part 104 of the tube so as to face each other, and fluid which is injected from the proximal end part 102 of the tube and flows up to the distal end part 104 of the tube may be sprayed to both sides through the two openings 120.

At this time, the guide member with an inclined part is disposed in the tube 100 in order to guide the direction of the fluid sprayed through the openings 120. The inclined part of the guide member serves to guide the fluid sprayed through the opening 120 toward the front, i.e. the distal side.

The guide member may be extended from the electrode tip 300 to the position where the opening 120 is formed. In the present embodiment, the guide member is formed as one body with the electrode tip 300. However, the present disclosure is not limited thereto, and a separate guide member may be coupled to the electrode tip 300.

Specifically, the guide member may include a cylinder part 310 and an inclined part 320 tapered from the cylinder part 310. The cylinder part 310 may be extended from the distal end part of the tube 100 to the distal end part of the opening 120. In particular, the cylinder part 310 may have an external diameter corresponding to the internal diameter of the distal end part 104 of the tube such that fluid does not flow to the distal side over the opening 120. The inclined part 320 may be extended from the distal end part of the opening 120 to the center of the opening 120. The inclined part 320 may be conical. In particular, the inclined part 320 may have an inclination of 20 to 60° with respect to the central axial line of the tube 100. However, the present disclosure is not limited thereto, and the inclined part may include various embodiments having an inclination, such as a polygonal tip.

Therefore, fluid which is injected from the proximal end part 102 of the tube and flows to the distal end part 104 of the tube may be sprayed through the opening 120, while the direction thereof is smoothly guided to the front along the inclined part 320. That is, according to the related art, fluid may be irregularly sprayed as the speed thereof is reduced by collision with the electrode tip. In accordance with the present embodiment, however, fluid may be pressurized and sprayed at high speed without interference while being smoothly guided to the forward outside by the inclined part 320.

Next, a medical device 2 in accordance with a second embodiment of the present disclosure will be described with reference to FIGS. 4 to 7.

The medical device 2 in accordance with the second embodiment of the present disclosure may roughly include a tube 2100, a handle part 2200, an electrode tip 2300, a fluid injection part 2500, an electrical energy supply part 2600, a guide member, a wire manipulation part 2700 and a wire 2800.

The tube 2100 may serve to transfer fluid and pass fluid therethrough, and is extended to have a proximal end part 2102 and a distal end part 2104. The handle part 2200 is coupled to the proximal end part 2102 of the tube, and the electrode tip 2300 is coupled to the distal end part 2104 of the tube. The electrode tip 2300 serves to receive electrical energy and form a puncture by cauterizing an interior part of the body of the patient, and is coupled to the distal end part 2104 such that at least a part thereof protrudes from the distal end part 2104 of the tube.

In the present embodiment, the wire manipulation part 2700 is slidably installed on the handle part 2200. The wire manipulation part 2700 corresponds to a part for manipulating the wire 2800 as described below, and a distal end part of the wire 2800 may be connected to the wire manipulation part 2700 to pull or push the wire 2800. Specifically, the handle part 2200 may have a hole with a predetermined length, and the wire manipulation part 2700 may be slidably installed through the hole. However, the present disclosure is not limited thereto, but the wire manipulation part may be rotatably installed on the handle part.

Figure 5:
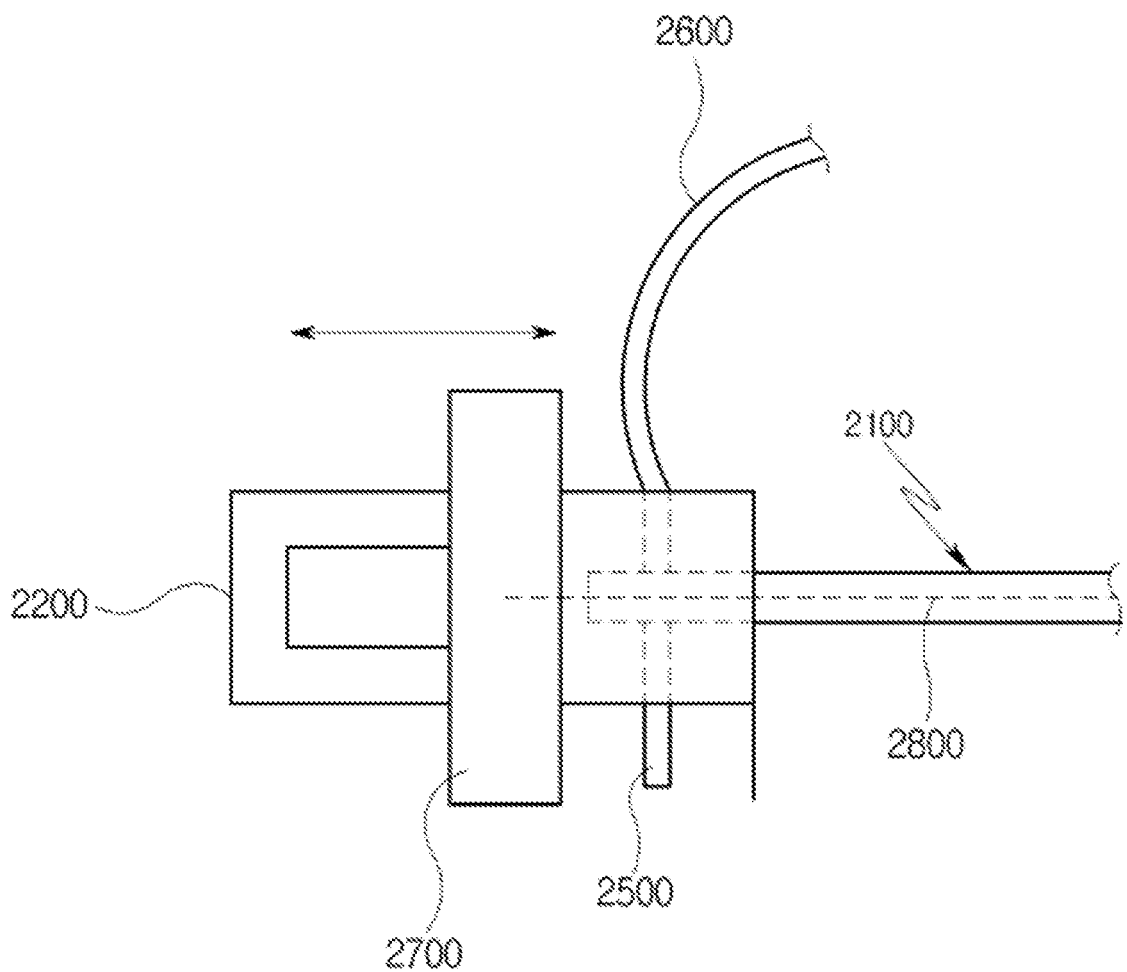
FIG. 5 is an expanded front view illustrating a proximal end part of FIG. 4.

The fluid injection part 2500 corresponds to a part for injecting fluid into the tube 2100. As illustrated in FIG. 5, the tube 2100 in accordance with the present embodiment is extended to the inside of the handle part 2200, and the fluid injection part 2500 is also extended to the inside of the handle part 2200 so as to communicate with the tube 2100.

The electrical energy supply part 2600 corresponds to a part for supplying electrical energy to the electrode tip 2300, and RF electrical energy generated through an RF generator may be supplied to the electrode tip 2300 through the electrical energy supply part 2600.

As illustrated in FIG. 5, the electrical energy supply part 2600 in accordance with the present embodiment may be extended to the inside of the handle part 2200 and electrically connected to the tube 2100. Therefore, RF electrical energy may be transferred from the electrical energy supply part 2600 to the electrode tip 2300 through the tube 2100, and applied to an interior part of the body of the patient through the electrode tip 2300 so as to form a puncture through the interior part.

Figure 6:
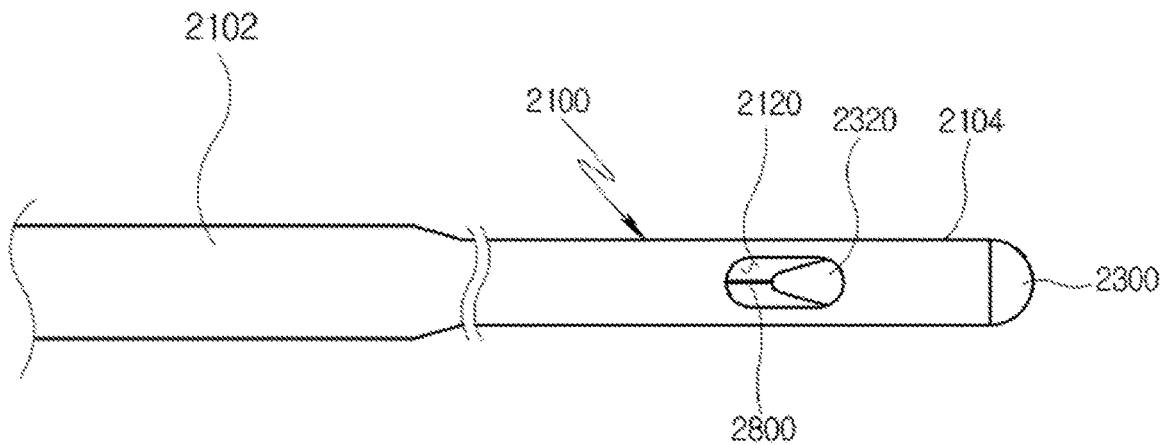
FIG. 6 is an expanded front view illustrating a distal end part of FIG. 4.
Figure 7:
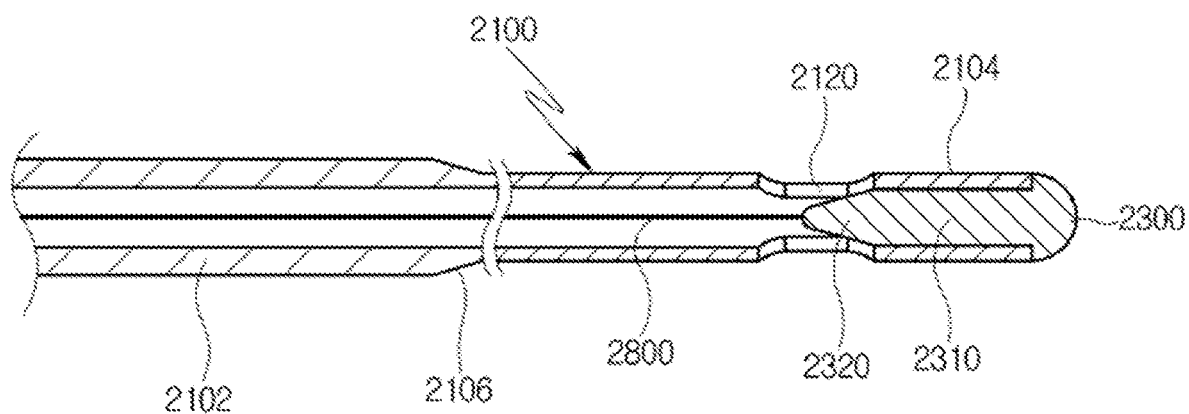
FIG. 7 is a cross-sectional view of FIG. 6.

Referring to FIGS. 6 and 7, the structure for spraying fluid, injected into the tube 2100 through the fluid injection part 2500, to the outside of the tube 2100 may be configured as described with reference to the first embodiment.

The tube 2100 may have one or more openings 2120, and the fluid within the tube 2100 may be sprayed to the outside through the openings 2120. At this time, the guide member with an inclined part is disposed in the tube 2100 in order to guide the direction of the fluid sprayed through the openings 2120. The guide member may be extended from the electrode tip 2300 to the position where the opening 2120 is formed. In the present embodiment, the guide member is formed as one body with the electrode tip 2300. Specifically, the guide member may include a cylinder part 2310 and an inclined part 2320 tapered from the cylinder part 2310. Therefore, fluid which is injected from the proximal end part 2102 of the tube and flows to the distal end part 2104 of the tube may be sprayed through the openings 2120, while the direction thereof is smoothly guided to the front along the inclined part 2320.

The medical device 2 in accordance with the present embodiment further includes a wire 2800 which has one end connected to the electrode tip 2300 or the distal end part 2104 of the tube and the other end extended to the handle part 2200, for a steering function. In the present embodiment, the proximal end part of the wire 2800 is connected to the wire manipulation part 2700, and the distal end part of the wire 2800 is connected to an end of the electrode tip 2300, i.e. an end of the inclined part 2320. Thus, when a user pulls the wire manipulation part 2700 toward the user, the distal end part 2104 of the tube is further bent toward the user, while the wire 2800 connected to the end of the electrode tip 2300 is pulled together.

For this operation, as illustrated in FIG. 7, at least a section 2106 of the tube 2100 may be tapered so that the proximal end part 2102 has a smaller thickness than the distal end part 2104. The present disclosure is not limited thereto. However, FIG. 7 illustrates that the proximal end part 2102 of the tube has a thickness twice larger than the thickness of the distal end part 2104 of the tube. Therefore, the flexibility of the proximal end part 2102 of the tube may be increased so that the distal end part 2104 of the tube can be bent, while the rigidity of the proximal end part 2102 of the tube is maintained.

Figure 8:
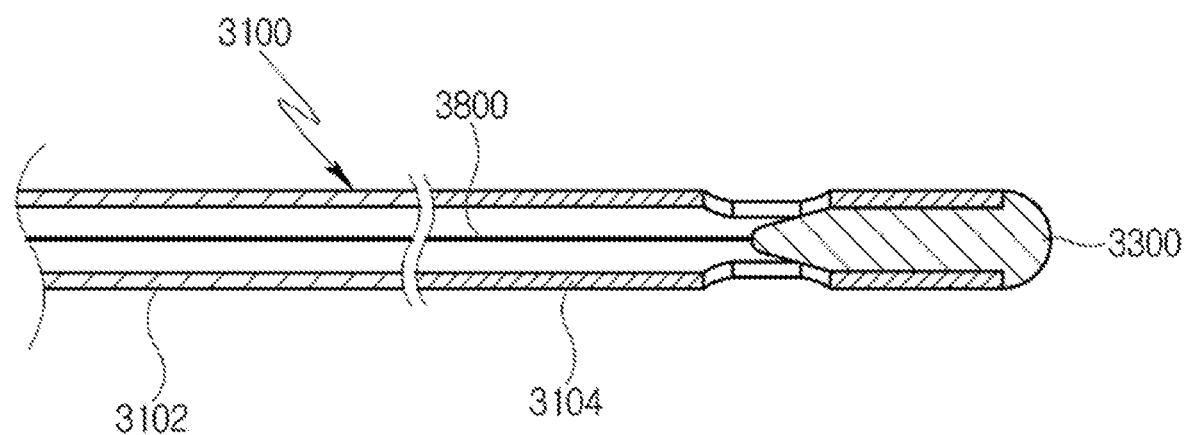
FIG. 8 is an expanded cross-sectional view illustrating a distal end part of a medical device in accordance with still another embodiment of the present disclosure.

Next, a medical device in accordance with a third embodiment of the present disclosure will be described with reference to FIG. 8. The medical device in accordance with the third embodiment of the present disclosure has the same structure as the medical device in accordance with the second embodiment of the present disclosure except only the structure of the tube of the medical device 2. Thus, the following descriptions will be focused on the tube.

In the present embodiment, a tube 3100 may include a first tube 3102 to which a handle part is coupled and a second tube 3104 to which an electrode tip 3300 is coupled. The first tube 3102 may be formed of a rigid material and the second tube 3104 may be formed of a flexible material. At this time, the first tube 3102 corresponds to the proximal end part of the tube, and the second tube 3104 corresponds to the distal end part of the tube. Therefore, the proximal end part of the tube may retain rigidity to provide column strength, but the distal end part of the tube may provide flexibility so as to be bent. When a user pulls a wire manipulation part toward the user, the second tube 3104 may be further bent toward the user while a wire 3800 connected to the end of the electrode tip 3300 is pulled together. For example, the first tube 3102 may be formed of stainless steel, and the second tube 3104 may be formed of nickel titanium alloy such as NITINOL.

Hereafter, a method using the medical device 1 in accordance with the first embodiment of the present disclosure will be described with reference to FIGS. 9 to 10. In the present embodiment, an interior part of the body of a patient, in which a puncture is to be formed, corresponds to tissue within the heart of the patient, for example, an interauricular septum 10 of the heart. Such a target part may be accessed through an inferior vena cautery (IVC), for example, a femoral vein.

Figure 9:
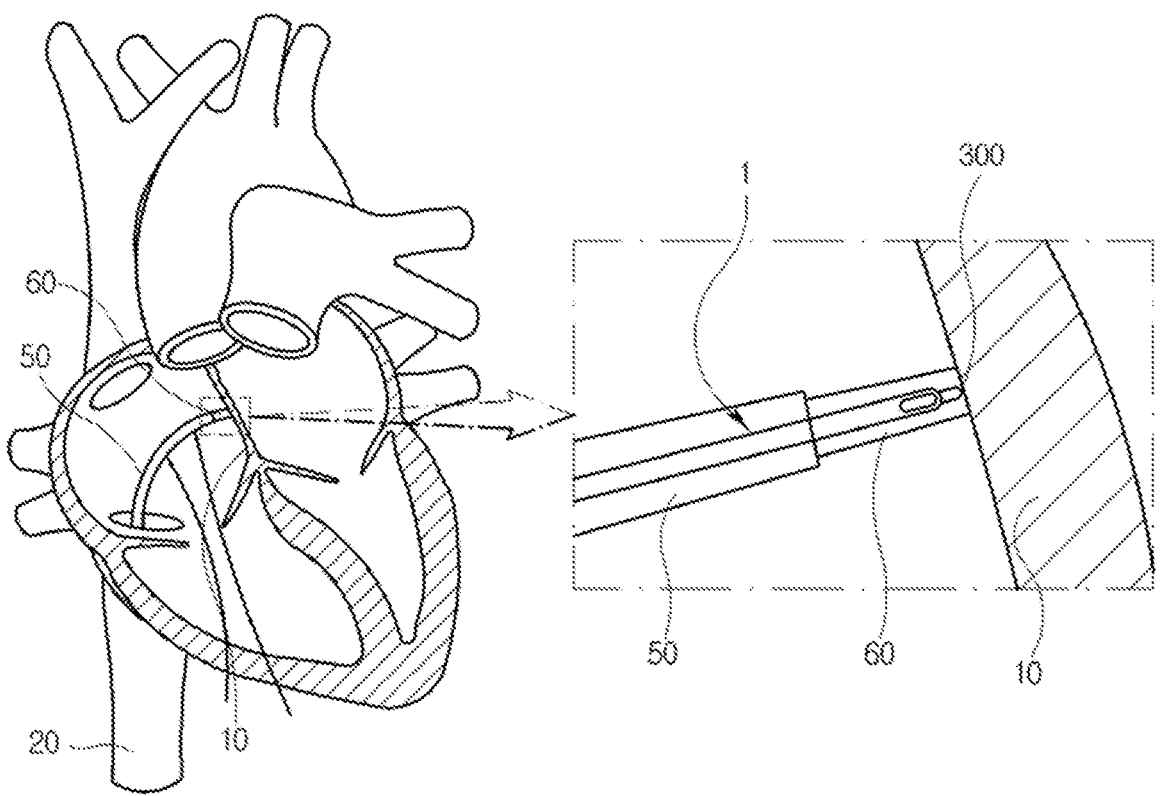
FIGS. 9 and 10 are diagrams illustrating a method which uses the medical device in accordance with the embodiment of the present disclosure.

First, referring to FIG. 9, the user may insert a sheath 50 and a dilator 60 into the right atrium of the heart through an inferior vena cautery 20. Specifically, the user may introduce a guide wire into the femoral vein, for example, the right femoral vein and insert the guide wire into the heart, and then insert the sheath 50 and the dilator 60 into the heart along the guide wire. Then, the guide wire may be removed, the medical device 1 in accordance with the present embodiment may be inserted into the sheath 50 and the dilator 60, and the user may decide the position of the dilator 60 such that the distal end part of the dilator 60 abuts on the interauricular septum 10 corresponding to a target part. At this time, the position of the electrode tip 300 of the medical device 1 may be adjusted to the position of the distal end part of the dilator 60. In order to easily adjust the position, the electrode tip 300 may be formed of platinum (Pt) or iridium (Ir). That is because, since Pt and Ir correspond to an X-ray opaque material, the user can easily check the position of the electrode tip 300 under the radioscopy. Since visibility can be secured, the user can easily decide the position of the electrode tip 300.

When the distal end part of the dilator 60 is disposed with respect to the oval fossa of the interauricular septum 10, the electrode tip 300 supplies electrical energy to the electrode tip 300 while contacted with the interauricular septum 10. That is, RF electrical energy generated by the RF generator is transferred from the electrical energy supply part 600 to the electrode tip 300 through the tube 100. Therefore, the energy may be transferred to the interauricular septum 10 by the electrode tip 300 to cauterize the interauricular septum 10, and a puncture is formed in the interauricular septum 10.

Figure 10:
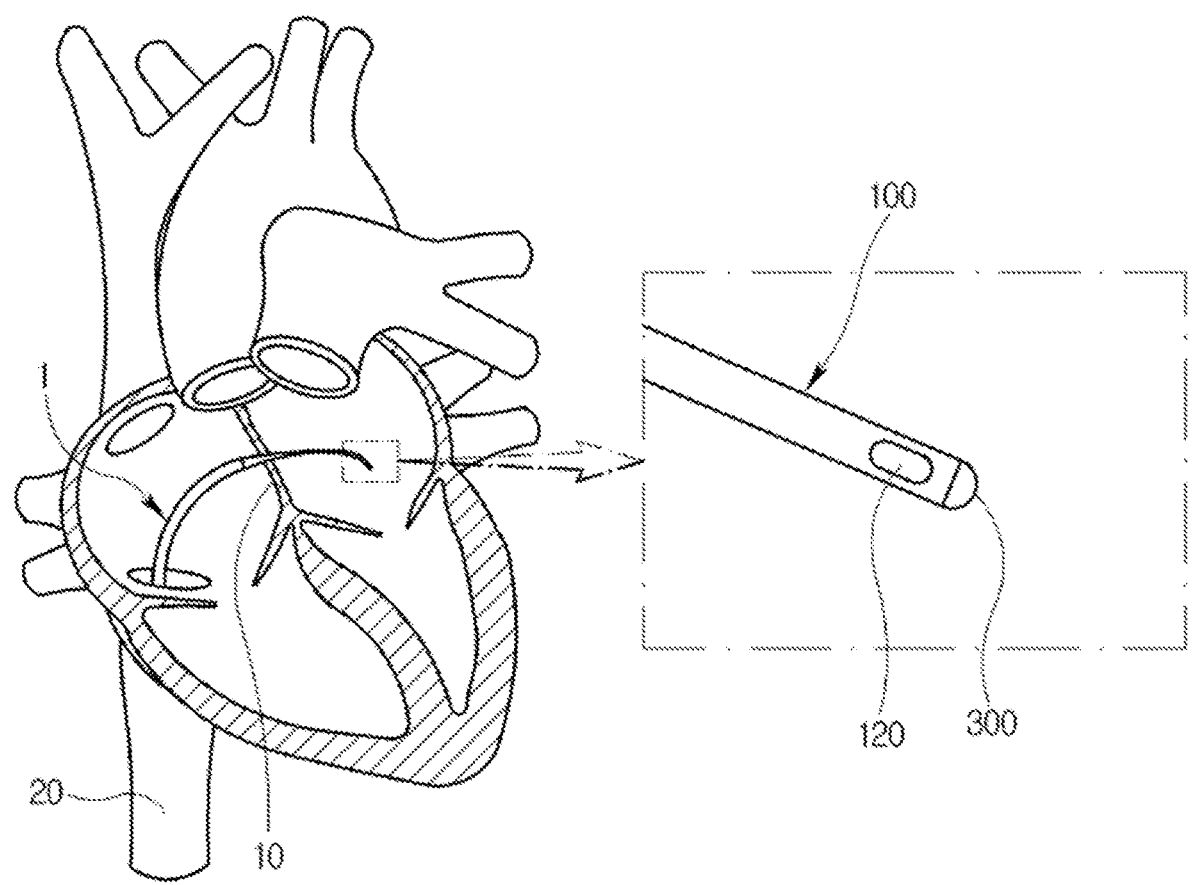

When the puncture is formed as illustrated in FIG. 10, the distal end part of the tube 100 of the medical device 1 may reach the left atrium through the puncture. Then, the energy transfer may be stopped, and fluid may be injected into the tube 100 through the fluid injection part 500. The fluid may be a contrast medium, for example. The contrast medium injected into the tube 100 may be transferred to the distal end part 104 of the tube, and injected into the left atrium through the opening 120. At this time, the fluid sprayed through the opening 120 may be smoothly induced toward the forward outside by the guide member, and effectively sprayed.

While various embodiments have been described above, it will be understood to those skilled in the art that the embodiments described are by way of example only. Accordingly, the disclosure described herein should not be limited based on the described embodiments.

What is claimed is:

1. A medical device comprising:
a tube through which fluid flows;
a handle part coupled to a proximal end part of the tube;
an electrode tip coupled to a distal end part of the tube;
a fluid injection part configured to inject the fluid into the tube;
one or more openings formed in the tube; and
a guide member disposed in the tube, the guide member having an inclined part to guide a direction of the fluid sprayed out through the one or more openings,
wherein the guide member is extended from the electrode tip to a position where the one or more openings are formed.

2. The medical device of claim 1, wherein the guide member is formed as one body with the electrode tip.

3. The medical device of claim 1, wherein the inclined part of the guide member is conical.

4. The medical device of claim 1, wherein the inclined part of the guide member has an inclination of 20 to 60° with respect to a central axial line of the tube.

5. The medical device of claim 1, wherein the guide member comprises a cylinder part,
wherein the inclined part is tapered from the cylinder part such that a diameter of the inclined part is constantly narrowed from the cylinder part.

6. The medical device of claim 5, wherein the inclined part is extended from one end of the one or more openings to a center of the one or more openings.

7. The medical device of claim 1, wherein the electrode tip is formed of an X-ray opaque material.

8. The medical device of claim 1, wherein the tube is coated with an insulator through dip coating, spray coating or heat shrink tubing.

9. The medical device of claim 1, further comprising a wire having a first end connected to the electrode tip or the distal end part of the tube and a second end extended to the handle part.

10. The medical device of claim 9, further comprising a wire manipulation part slidably or rotatably mounted on the handle part,
wherein the second end of the wire is connected to the wire manipulation part.

11. The medical device of claim 9, wherein at least a section of the tube is tapered so that the proximal end part of the tube has a smaller thickness than the distal end part of the tube.

12. The medical device of claim 9, wherein the tube comprises a first tube to which the handle part is coupled and a second tube to which the electrode tip is coupled,
wherein the first tube is formed of a rigid material, and the second tube is formed of a flexible material.

* * * * *